US007765843B2

(12) United States Patent
Park

(10) Patent No.: US 7,765,843 B2
(45) Date of Patent: Aug. 3, 2010

(54) FLEXIBLE ROD MANUFACTURING APPARATUS AND METHOD FOR A SPINAL FIXATION AND THE FLEXIBLE ROD MANUFACTURED THROUGH THE SAME

(76) Inventor: Kyung-Woo Park, 995-25 Daechi 3-dong, Kangnam-gu, Seoul (KR) 135-283

( * ) Notice: Subject to any disclaimer, the term of this patent is extended or adjusted under 35 U.S.C. 154(b) by 258 days.

(21) Appl. No.: 11/851,104

(22) Filed: Sep. 6, 2007

(65) Prior Publication Data

US 2008/0065071 A1 Mar. 13, 2008

(30) Foreign Application Priority Data

Sep. 7, 2006 (KR) ..................... 10-2006-0086345

(51) Int. Cl.
*B21F 3/02* (2006.01)
*B21D 11/14* (2006.01)

(52) U.S. Cl. .......................................... 72/135; 72/299

(58) Field of Classification Search ..................... 72/64, 72/135, 124, 298, 299, 371, 422, 424
See application file for complete search history.

(56) References Cited

U.S. PATENT DOCUMENTS 5,875,666 A * 3/1999 Itaya ........................... 72/140
6,094,957 A * 8/2000 Masunaga et al. ............. 72/128
7,134,305 B2 * 11/2006 Wu ............................. 72/144
2004/0154365 A1 8/2004 Tsuritani

* cited by examiner

*Primary Examiner*—Dana Ross
*Assistant Examiner*—Teresa M Bonk
(74) *Attorney, Agent, or Firm*—Lowe Hauptman Ham & Berner LLP

(57) ABSTRACT

The present invention relates to a rod capable of securely connecting pedicle screws in a pedicle screw system for correcting a damaged or transformed spine and a method and an apparatus for fabricating the same and, more particularly, to a flexible pedicle rod with superelasticity in order to provide a flexibility to a fixation between spine segments and a method and an apparatus capable of fabrication the same in mass production. The apparatus according to the present invention comprises a body; an X- and Y-axis moving element mounted on a top surface of the body, the X- and Y-axis moving element simultaneously moving in X-axis and Y-axis directions to wind a material at an angle of 90 degrees; a magazine mounted on the X- and Y-axis moving element to load a material; a material withdrawing element for withdrawing materials one by one from the magazine; and a material molding element mounted on the X- and Y-axis moving element, the material molding element gripping both ends of the material withdrawn from the material withdrawing element and rotating to mold a portion of the material in a spring shape.

4 Claims, 7 Drawing Sheets

FLEXIBLE ROD MANUFACTURING APPARATUS AND METHOD FOR A SPINAL FIXATION AND THE FLEXIBLE ROD MANUFACTURED THROUGH THE SAME

BACKGROUND OF THE INVENTION

The present invention relates to a rod capable of securely connecting pedicle screws in a pedicle screw system for correcting a damaged or transformed spine and a method and an apparatus for fabricating the same and, more particularly, to a flexible pedicle rod with superelasticity in order to provide flexibility to a fixation between spine segments and a method and an apparatus capable of fabricating the same in mass production.

Generally, when the spine undergoes bad environments of artificial factors and degenerative spine disease and is maintained in abnormal postures for a long time, serious back pain is induced by the press of the nerve system passing through the spinal canal.

In general, in the case where the conservative treatment has an effect on the patients with degenerative spine disease, the patients need the surgical treatment. Particularly, a spinal fusion treatment is carried out in spinal stenosis, spondylolisdthesis and spondylolysis accompanying instability between spinal segments. A conventional surgical treatment to use a rigid rod, which does not have mobility at all, gives rise to many side effects on the patients as time goes on. Therefore, a pedicle fixing apparatus is to be inserted into an injured or wrenched site of the spine in order that the injured or wrenched site is neither suppressed nor is ruined or the part thereof is not pressed or pushed down.

As shown in FIGS. 1 and 2, a conventional pedicle fixing apparatus includes a plurality of pedicle screws 200 which are respectively inserted, as a supporting member, through the pedicle into injured or deformed vertebra, wherein each of the pedicle screws 200 has a head 201 with a U-shaped rod passage 201*a*; rods 250 for making a correction of the pedicle through an interconnection between the pedicle screws 200; set screws 300 to be inserted into the rod passage 201*a* for fixing the rods 250; and a transverse link 400 for holding a pair of the rods 250.

In the pedicle fixing apparatus of FIG. 1, the rod plays an important role in the fixation of the deformed vertebra. Therefore, the quality of the material, elasticity, and so on, of the rod has a significant influence on the human body.

Since most conventional rods are formed out of a titanium material for a medical treatment, the rods themselves do not have elasticity. There is a problem in that it is difficult to maintain a normal waist curve because the fusion of the spine segments is conducted according to the shape of the rod after the surgical spine correction. Moreover, after the spine completely fuses to the arrangement form of the rod, since a load is concentrated on the upper segment or the lower segment of the spine into which the pedicle screws are inserted, instability and another stenosis can be caused after several years.

To solve the demerit of the rigid rod, various methods to partially provide elasticity to a part of the rod have been introduced. Particularly, in order to solve the demerit of the conventional rods effectively and to make the surgical correction of spinal deformity easy, the applicant of the present invention introduced a rod for the pedicle fixation using a shape memory alloy such as a Ni—Ti alloy (Nitinol) which is harmless in the human body with high congeniality and has the property similar to the human tissue in superelasticity and absorption nature. For example, the various rods have been introduced in Korean patent application Nos. 2004-76105, 2004-76106, 2004-97833 and 2004-97834.

As shown in FIGS. 3*a* and 3*b*, a rod (600) described in the cited references has a body 602 and an elastic member 604, which has a coil type formed in the middle of the body 602, to provide the flexibility to the rod 600. This flexible rod has a length of approximately 80 to 100 mm (typically, 82 mm) and a small standard diameter of approximately 3 to 6 mm. Since the material of the rod itself is to have the hard metal organization and the rod is to be manufactured in a coil type with the shape memory through a heating process, it is very difficult to form the elastic member of the coil type in the middle of the rod. The rod having the coil section is manually made due to the drawback to the manufacture of the rod; however, it is very difficult to make the rod uniform and it is impossible to realize the mass production and commercialization.

On the other hand, when the surgical correction of spinal deformity, in which two parts of the rod body are different from each other in height, is performed, the elastic member having a large volume causes a surgical inconvenience in the procedure of securing the rod within the pedicle screw because the body described in the cited references is positioned at the central axis of the elastic member and then the pedicle can be in contact with the elastic member. In this case, there is a problem in that an inevitable operation procedure which has to dig a space out of the spine is required.

SUMMARY OF THE INVENTION

Embodiments of the present invention are directed to providing an apparatus for fabricating a flexible rod of a pedicle screw system in mass production, wherein the fixation between spinal segments is improved after the surgical correction of spinal deformity and superelasticity is provided for a part of the flexible rod in order that an elastic power is induced when an external force is applied to the spine.

Also, embodiments of the present invention are directed to providing a rod of a pedicle screw system, which has no interference from a elastic section of the rod in the surgical correction of spinal deformity, by providing eccentricity between a rod body and the elastic section.

According to an aspect to the present invention, there is provided an apparatus for fabricating a flexible pedicle rod for pedicle fixation, the apparatus comprising a body; an X- and Y-axis moving element mounted on a top surface of the body, the X- and Y-axis moving element simultaneously moving in X-axis and Y-axis directions to wind a material at an angle of 90 degrees; a magazine mounted on the X- and Y-axis moving element to load a material; a material withdrawing element for withdrawing materials one by one from the magazine; and a material molding element mounted on the X- and Y-axis moving element, the material molding element gripping both ends of the material withdrawn from the material withdrawing element and rotating to mold a portion of the material in a spring shape.

According to another aspect to the present invention, there is provided a method for fabricating a flexible pedicle rod for pedicle fixation, the method comprising a first step of initializing; a second step of driving a feeder driving motor to move a feeder straight in the initialization state, thereby withdrawing a material from a magazine; a third step of gripping one end of the material moving straight by the feeder at the die; a fourth step of driving an Y-axis servo motor built in a body to move an Y-axis stage straight, thereby fixing the other end of the material to a groove shaft of a fixing base; a fifth step of driving a high-frequency heater to heat the material at a predetermined temperature; a sixth step of respectively driving Y-axis and X-axis servo motors in Y-axis and X-axis directions to wind the material fixed to the die and the groove shaft at 90 degrees; a seventh step of driving the X-axis servo motor to move an X-axis stage in the X-axis direction, and driving a rotating motor mounted on the X-axis stage to wind the material fixed to the fixing base on a spiral line and wind the material in a coil shape; and an eighth step of discharging the material.

According to still another aspect to the present invention, there is provided a flexible pedicle rod prepared by a process comprising a first step of initializing; a second step of driving a feeder driving motor to move a feeder straight in the initialization state, thereby withdrawing a material from a magazine; a third step of gripping one end of the material moving straight by the feeder at the die; a fourth step of driving an Y-axis servo motor built in a body to move an Y-axis stage straight, thereby fixing the other end of the material to a groove shaft of a fixing base; a fifth step of driving a high-frequency heater to heat the material at a predetermined temperature; a sixth step of respectively driving Y-axis and X-axis servo motors in Y-axis and X-axis directions to wind the material fixed to the die and the groove shaft at 90 degrees; a seventh step of driving the X-axis servo motor to move an X-axis stage in the X-axis direction, and driving a rotating motor mounted on the X-axis stage to wind the material fixed to the fixing base on a spiral line and wind the material in a coil shape; and an eighth step of discharging the material.

According to still another aspect to the present invention, there is provided a flexible pedicle rod comprising a straight-line portion, wherein one end of the straight-line portion is formed on a straight line and the other end of the straight-line portion is formed on the same straight line; and a spring-shaped elastic portion wound in a spiral shape at a predetermined portion between the straight-line portions, wherein the elastic portion and the rod body are formed to be eccentric by a predetermined interval.

As described in one embodiment of the present invention, a major feature of the present invention is to produce in large quantities of pedicle rods each having a coil-shaped elastic portion from the conventional rigid rod with no elasticity.

BRIEF DESCRIPTION OF THE DRAWINGS

The above and other aspects, features and other advantages of the subject matter of the present disclosure will be more clearly understood from the following detailed description taken in conjunction with the accompanying drawings, in which.

DETAILED DESCRIPTION OF THE PREFERRED EMBODIMENTS

Hereinafter, exemplary embodiments of the present invention will be described with reference to accompanying drawings.

A apparatus and a method for fabricating a flexible pedicle rod for pedicle fixation according to one embodiment of the present invention are implemented to produce in large quantities of pedicle rods in the state that a superelastic force is applied to a portion of each of the pedicle rods.

A material for a pedicle rod used for the apparatus according to the one embodiment of the present invention is fabricated using a shape-memory alloy that does not harm human beings in various types of shape-memory alloys, particularly Nitinol (i.e., Ni—Ti alloy). The present invention is not limited to a pedicle rod using Nitinol. That is, a metal that does not harm human beings, e.g., a titanium-based metal (including an alloy), a stainless 316 (SUS 316) metal or the like may also be used to fabricate a pedicle rod according to one embodiment of the present invention.

Figure 1:
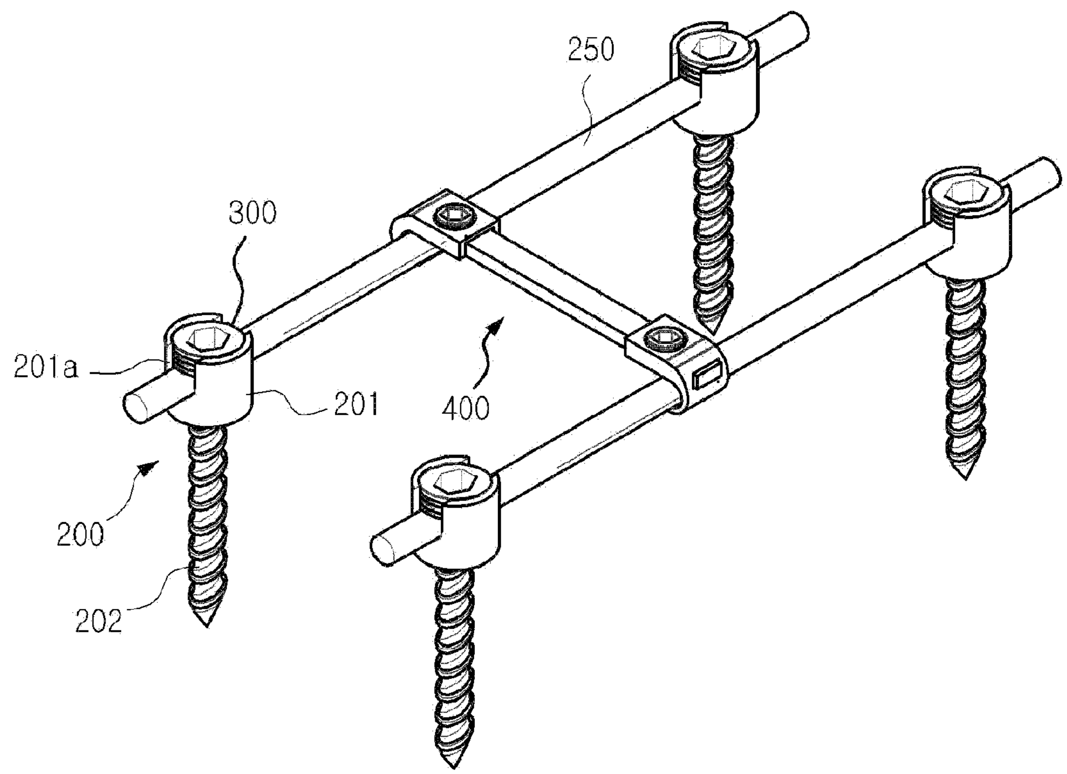
FIG. 1 is a perspective view of a conventional pedicle fixing apparatus having a pedicle screw system for a surgical correction of spinal deformity.
Figure 2:
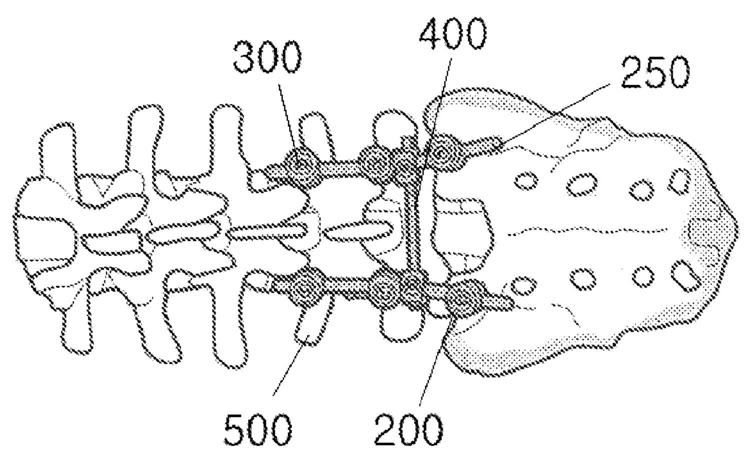
FIG. 2 is a perspective view of a conventional pedicle fixing apparatus installed in vertebrae lumbales.
Figure 3A:
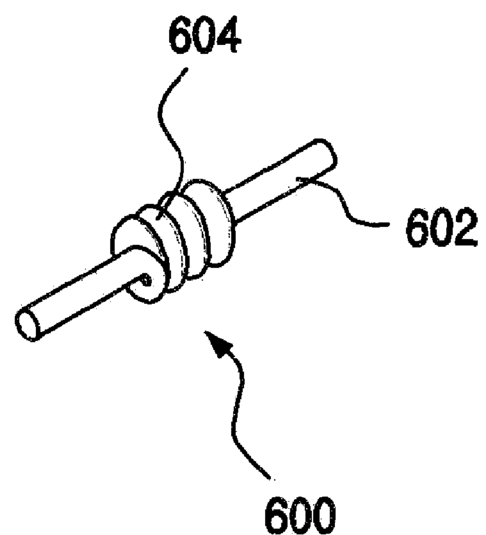
FIGS. 3*a* and 3*b* are views illustrating flexible pedicle rods used in the conventional pedicle fixing apparatus.
Figure 3B:
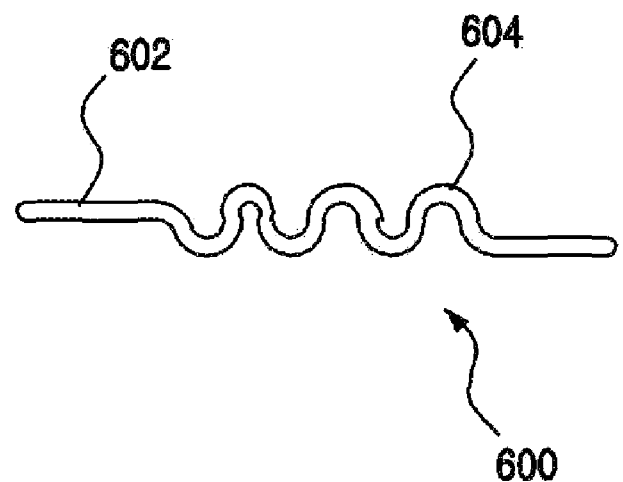
Figure 4:
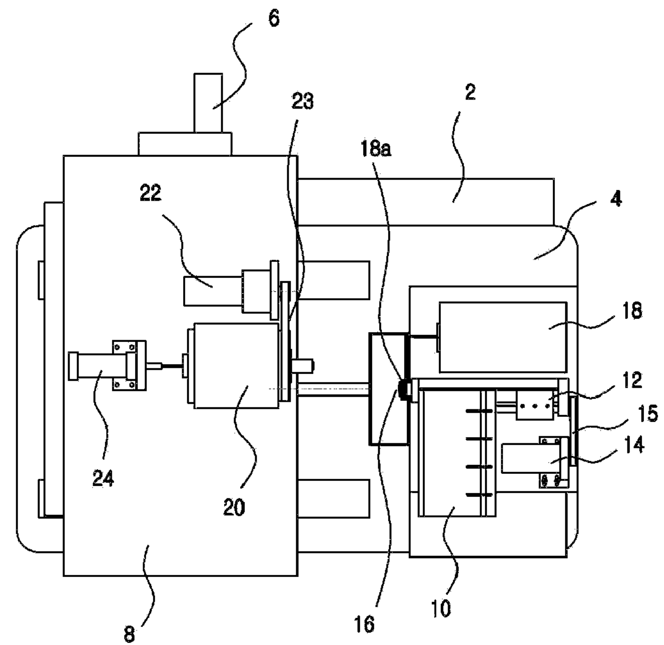
FIGS. 4 to 6 are front, right lateral and left lateral views of an apparatus for fabricating a flexible pedicle rod according to the present invention.
Figure 5:
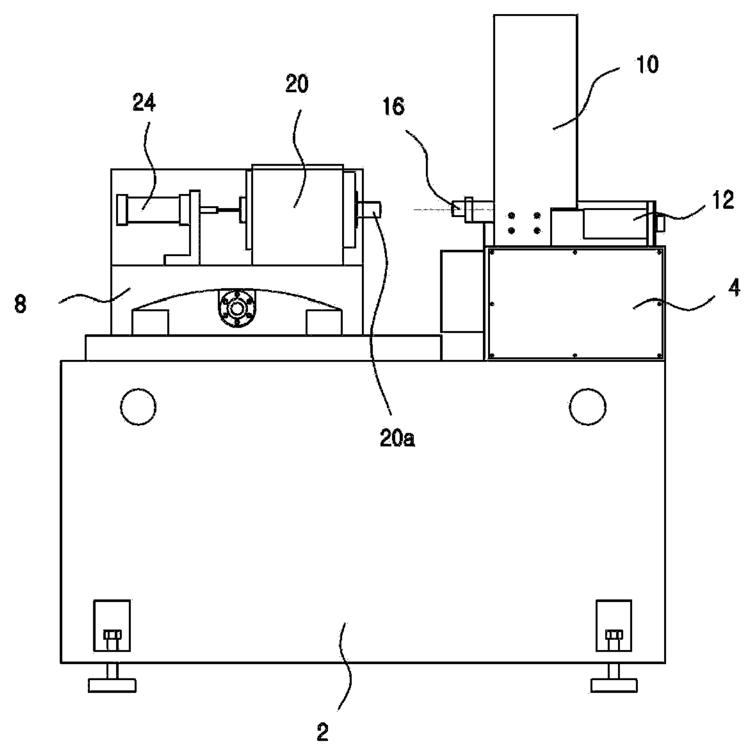
Figure 6:
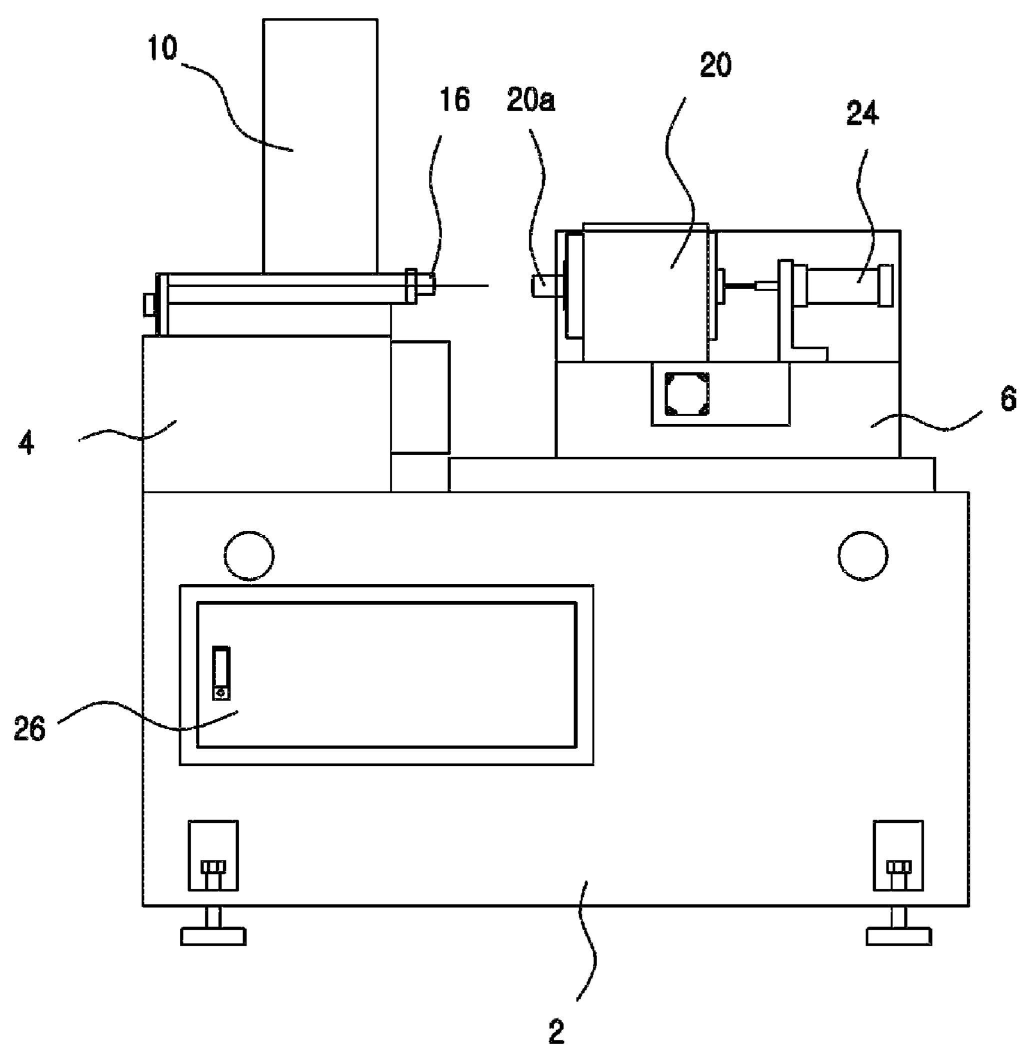

As illustrated in FIGS. 4 to 6, an apparatus for fabricating a flexible pedicle rod includes a body 2 having a Y-axis servo motor (not shown) built therein; a Y-axis stage 4 mounted on a top surface of the body 2 to move in a Y-axis direction by means of a driving force of the Y-axis servo motor; an X-axis servo motor 6 mounted on one side of the body 2; an X-axis stage 8 mounted on the Y-axis stage 4 to move in an X-axis direction by means of a driving force of the X-axis servo motor; a magazine 10 mounted on the Y-axis stage 4 at a predetermined inclination angle to load a material; a feeder 12 mounted at a rear end of the magazine 10 to withdraw materials loaded to the magazine 10 by moving them forward one by one; a feeder driving motor 14 for providing rotation power to the feeder 12 such that the feeder 12 can move forward; a first timing belt 15 for connecting between the feeder 12 and the feeder driving motor 14 to deliver power; a die 16 mounted in front of the feeder 12 to grip a rear end of a material supplied by means of the operation of the feeder 12; a high-frequency heater 18 mounted at one side of the feeder 12 to provide a predetermined heat source to a material through a coil 18*a* wound on an outer circumferential surface of the die 16 and then moving to a heating position of the material by means of a driving force of the Y-axis servo motor 6; a fixing base 20 mounted on the Y-axis stage 4 and having a groove shaft 20*a* mounted at a front side of the fixing base 20, the groove shaft supporting a material by fixing the other end of the material thereto; a C-axis motor 22 for providing a rotation force to the fixing base 20 to wind a material in a spiral shape; a second timing belt 23 for connecting between the groove shaft 20*a* of the fixing base 20 and the C-axis motor 22 to deliver power; and a cylinder 24 mounted at a rear of the fixing base 20 to discharge a molded material from the groove shaft 20*a* by moving straight toward the groove shaft 20*a*. Reference numeral 26 denotes a controller panel.

In the aforementioned configuration, since the C-axis motor 22 is positively and reversely rotatable, an elastic portion formed in the material can be molded in the shape of a string wound in a left or right direction.

Figure 7:
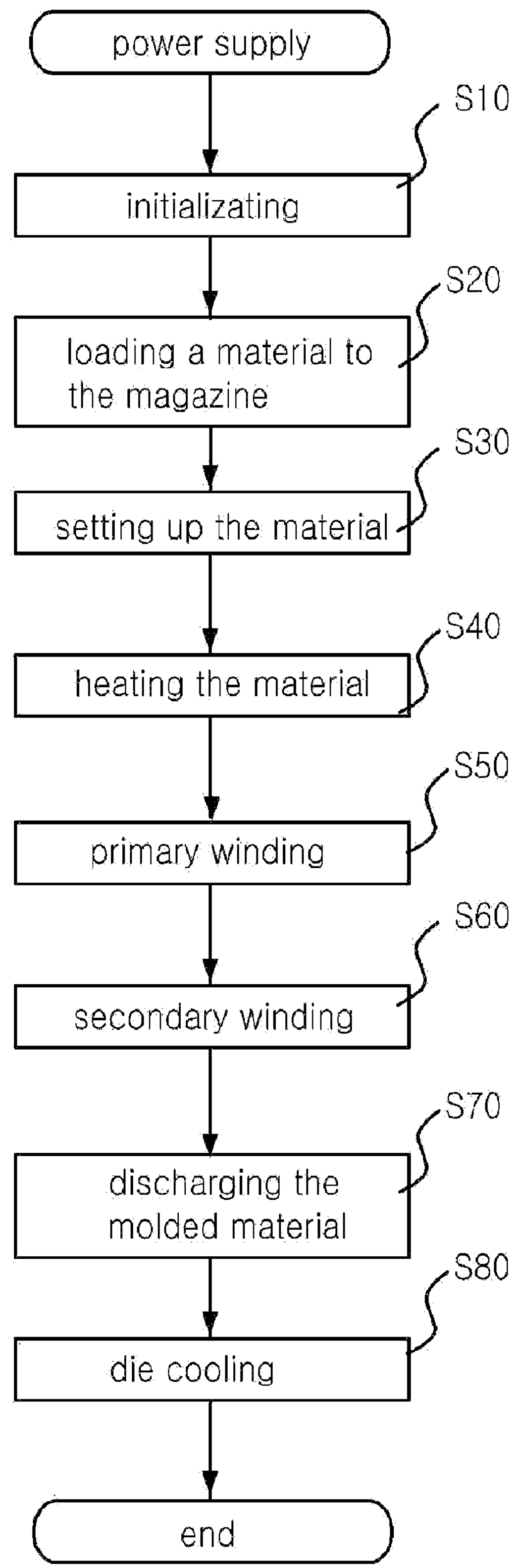
FIG. 7 is a flow chart illustrating a method for fabricating the flexible pedicle rod according to the present invention.

Hereinafter, fabricating processes using the apparatus for fabricating a flexible pedicle rod according to the one embodiment of the present invention will be described in detail with respect to FIGS. 7 and 8.

First, a power source switch (not shown) mounted on the controller panel 26 is turned on, thereby initializing the apparatus (S10). If the feeder driving motor 14 is operated after loading a material to the magazine 10 in the initial state of the apparatus, the feeder 12 moves straight to withdraw the material toward the die 16 (S20). One end of the withdrawn material is gripped by the die 16, and the other end of the withdrawn material is fixed to the groove shaft 20*a* of the fixing base 20 opposite to the die 16 on an axis line, thereby completing the setup of the material (S30) ((a) to (d) of FIG. 8).

In the embodiment of the present invention, an interval at which both ends of the material are gripped is about 15 mm.

Figure 8:
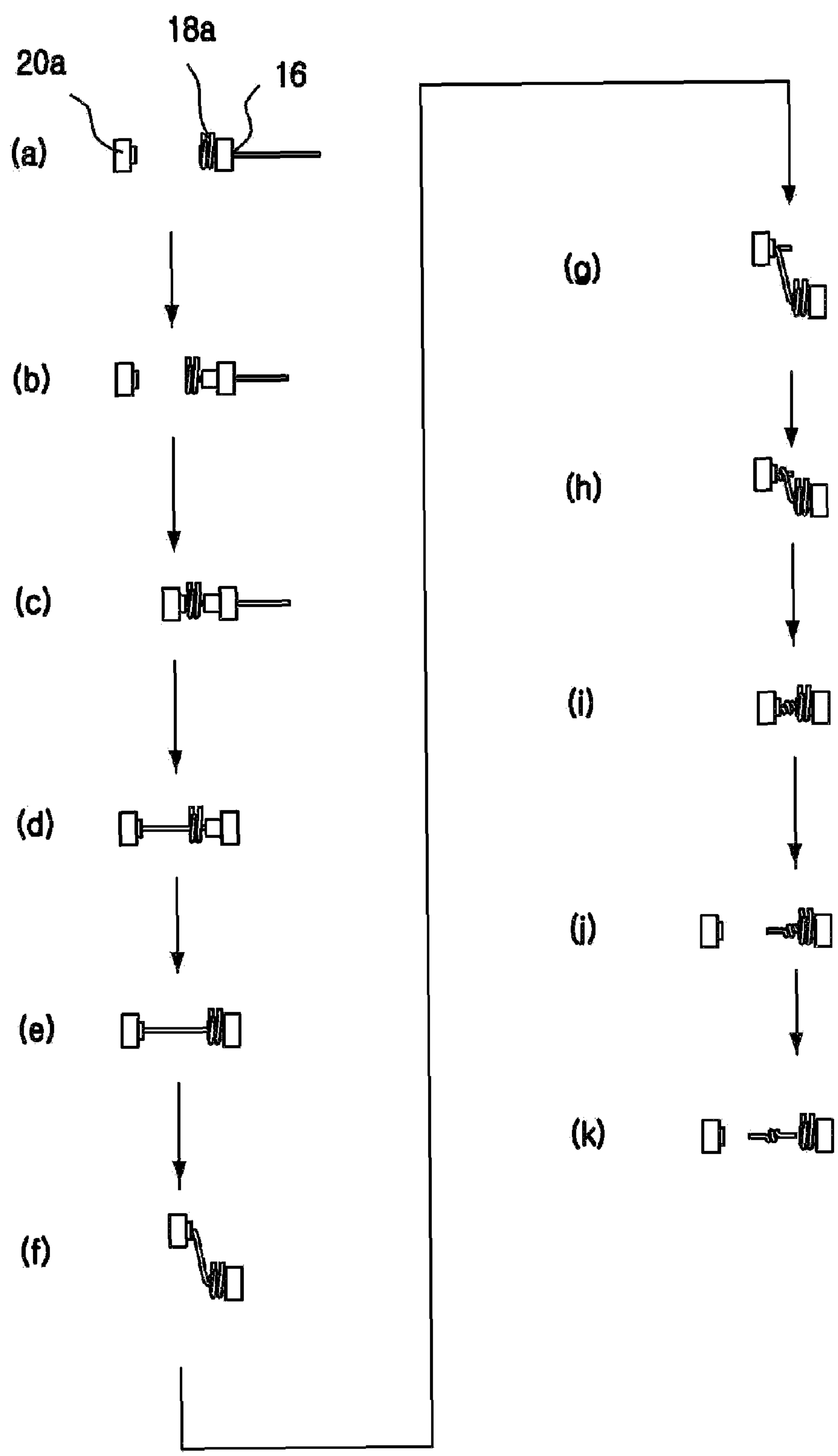
FIG. 8 is a schematic view illustrating a fabricating procedures of the flexible pedicle rod according to the present invention.

After completing the step S30, the high-frequency heater 18 and the coil 18*a* of the high-frequency heater 18 heat the material withdrawn from the die 16 while moving by means of the operation of the Y-axis servo motor (S40) ((c) and (d) of FIG. 8). At this time, The temperature at which the material is heated by the high-frequency heater 18 is about 600 to 700° C. If the heating temperature of the material is 600° C. or less, it is difficult to obtain a molded product having a desired shape. If the heating temperature of the material is 700° C. or more, a change in property of the material may be caused.

When the heating of the material is completed, the Y-axis and X-axis servo motors are simultaneously driven. Accordingly, the Y-axis and X-axis stages 4 and 8 move in the Y-axis and X-axis directions, respectively. Through the operations of the Y-axis and X-axis stages 4 and 8, the X-axis stage 8 is rotated in a direction of 90° about the die 16, and the material having both ends fixed to the die 16 and the groove shaft 20*a* of the fixing base 20 is primarily bent at an angle of 90° (S50) ((e), (f) and (g) of FIG. 8).

After completing the primary winding of the material, the C-axis motor 22 is rotated and driven, and the X-axis stage 8 moves and rotates the material three times on a spiral line, thereby performing a secondary winding (S60) ((h) and (i) of FIG. 8). Through the operation, the material forms an elastic portion in a spring shape through. At the step S50, since the C-axis motor 22 is positively and reversely rotatable, the elastic portion forms a spring wound in a right screw direction in a positive rotating operation, and forms a spring wound in a left screw direction in a reverse rotating operation.

After completing the spring molding of the material, a gripping force is eliminated from the die 16 ((j) of FIG. 8). The Y-axis stage 4 moves by driving the Y-axis motor, thereby leaving the material from the die 16. If the cylinder 24 moves straight to pass through the groove shaft 20*a* of the fixing base 20, the molded material fixed to the groove shaft 20*a* is discharged (S70) ((k) of FIG. 8).

After discharging the material as described above, compressed air is provided to the die 16 from the outside, thereby cooling the die 16 (S80).

Figure 9:
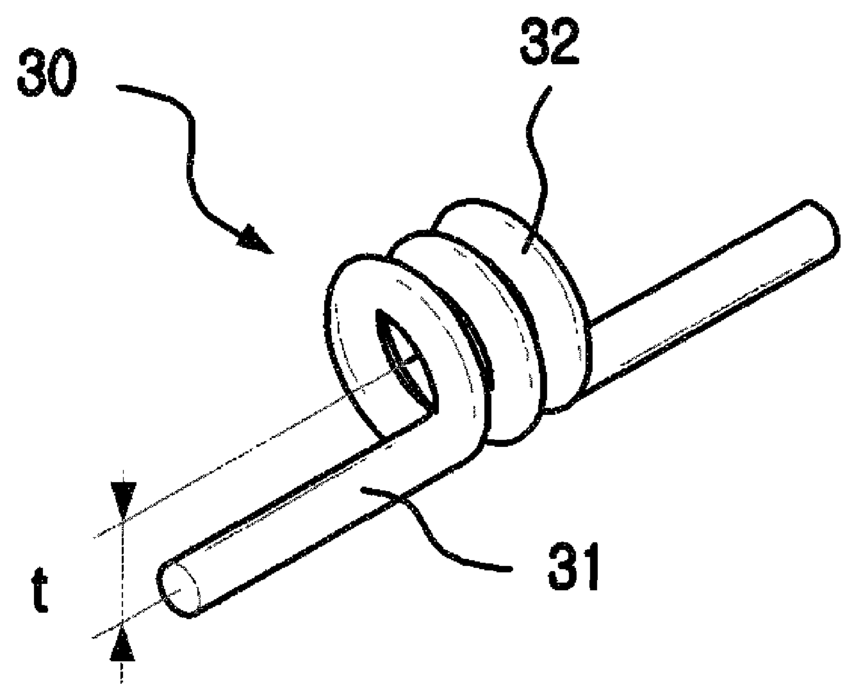
FIG. 9 is a perspective view of the flexible pedicle rod according to the present invention.

As illustrated in FIG. 9, a flexible pedicle rod 30 fabricated through the aforementioned configuration and fabricating method includes a rigid rod body 31 having a straight line shape and a flexible elastic portion 32 having a spring shape. At this time, the pedicle rod 30 is formed into an eccentric structure in which the center of the rod body 31 has a predetermined deviation t with respect to the center of the elastic portion 32. Since the heights of screws implanted into a pedicle are different from one another in a vertebral pedicle correcting operation, the pedicle rod 30 prevents the elastic portion 32 from being interfered by the pedicle when the pedicle rod 30 is seated on the pedicle. That is, when the pedicle rod 30 is fabricated in the state that the center of the rod body 31 is positioned on the same line with respect to the center of the elastic portion 32, a circumferential surface of the elastic portion 32 contacts the pedicle in the process of seating the pedicle rod 30 into a receiving groove of each of the screws with different heights. For this reason, it is difficult to seat the pedicle rod 30, and a vertebral bone may be unavoidably cut down by an interval at which the elastic portion 32 contacts the pedicle. However, since the elastic portion 32 can face upward in the pedicle rod 30 having eccentricity as described in the one embodiment of the present invention, interference between the elastic portion 32 and the pedicle does not occur.

In addition, since the flexible pedicle rod 30 is flexible only at the elastic portion 32 and the rod body 31 is a rigid part, three-dimensional flexibility can be provided even though an error occurs in the process of connecting the pedicle rod 30 after the implant of the pedicle screws.

As described above, according to one embodiment of the present invention, a pedicle rod having a relatively short length and a rigid property is provided with a flexible elastic portion, and it is possible to produce in large quantities of pedicle rods with such a structure, so that the pedicle rods can be remarkably commercialized in a pedicle correcting operation.

The pedicle rod provided with an elastic portion fabricated according to one embodiment of the present invention is deformed at a predetermined temperature and formed of a memory-shape alloy (nitanol) with superelasticity so that flexibility and durability can be maximized, and an operation can be easily performed due to flexibility caused at a deformation temperature of 10° C. or less, possessed by the shape-memory alloy. Further, the present invention provides a pedicle fixing apparatus using a pedicle rod provided with an elastic portion and a noble connection method for fixing the pedicle rod with segments, so that instability between spinal segments are cured, and exercise between the spinal segments can be maintained. In addition, a side effect of an operation using the conventional rigid rod can be reduced, and an operation can be easily performed.

Although preferred embodiments of the present invention have been described for illustrative purposes, those skilled in the art will appreciate that various modifications, additions and substitutions are possible, without departing from the scope and spirit of the invention as disclosed in the accompanying claims.

What is claimed is:

1. An apparatus for fabricating a flexible pedicle rod for pedicle fixation, comprising:

a body;

an X- and Y-axis moving element mounted on a top surface of the body, the X- and Y-axis moving element simultaneously moving in X-axis and Y-axis directions to bend a material at an angle of 90 degrees;

a magazine mounted on the X- and Y-axis moving element to load a material;

a material withdrawing element for withdrawing materials one by one from the magazine; and a material molding element mounted on the X- and Y-axis moving element, the material molding element gripping both ends of the material withdrawn from the material withdrawing element and rotating to mold a portion of the material in a spring shape, wherein the material withdrawing element includes:

a feeder mounted at a rear end of the magazine to withdraw materials loaded to the magazine by moving them forward one by one;

a feeder driving motor for providing rotation power to the feeder such that the feeder moves forward; and a first timing belt for connecting between the feeder and the feeder driving motor to deliver power; and wherein the material molding element includes:

a die mounted in front of the feeder to grip a rear end of a material supplied by means of the operation of the feeder;

a fixing base mounted on the X- and Y-axis moving element, the fixing base and having a groove shaft mounted at a front side of the fixing base, the groove shaft supporting a material by fixing the other end of the material thereto;

a C-axis motor for providing a positive/reverse rotation force to the fixing base to bend a material in the spring shape; and a second timing belt for connecting between the groove shaft of the fixing base and the C-axis motor to deliver power.

2. The apparatus of claim 1, wherein the X- and Y-axis moving element includes:

a Y-axis servo motor built in the body;

a Y-axis stage mounted on the top surface of the body to move in the Y-axis direction by means of a driving force of the Y-axis servo motor;

an X-axis servo motor mounted on one side of the body; and an X-axis stage mounted on the Y-axis stage to move in the X-axis direction by means of a driving force of the X-axis servo motor.

3. The apparatus of claim 1, further comprising a high-frequency heater which moves to a heating zone by driving force of the Y-axis motor, being installed at one end of the feeder.

4. The apparatus of claim 1, further comprising a cylinder mounted at a rear end of the fixing base to discharge a molded material from the groove shaft by moving straight forward the groove shaft.

* * * * *